US005472695A

United States Patent [19]
Neeman et al.

[11] Patent Number: 5,472,695
[45] Date of Patent: Dec. 5, 1995

[54] THERAPEUTIC APPLICATION OF A THYME EXTRACT AND IN - VITRO METHODS FOR INHIBITING THE GROWTH AND UREASE ACTIVITY OF HELICOBACTER PYLORI

[75] Inventors: Itzhak Neeman; Mina Tabak, both of Haifa; Robert Armon, Nesher, all of Israel

[73] Assignee: Technion Research and Development Foundation Ltd., Technion, Israel

[21] Appl. No.: 225,951

[22] Filed: Apr. 8, 1994

Related U.S. Application Data

[63] Continuation-in-part of Ser. No. 945,376, Sep. 16, 1992, abandoned.

[30] Foreign Application Priority Data

Jun. 25, 1992 [IL] Israel ........................................ 102313

[51] Int. Cl.$^6$ .................................................... A61K 35/78
[52] U.S. Cl. ...................... 424/195.1; 514/926; 514/927; 514/928
[58] Field of Search ........................ 424/195.1; 514/926, 514/927, 928

[56] References Cited

U.S. PATENT DOCUMENTS

| | | | |
|---|---|---|---|
| 4,803,069 | 2/1989 | Kékesi et al. ............................ | 424/74 |
| 5,252,344 | 10/1993 | Shi .......................................... | 424/682 |

OTHER PUBLICATIONS

H. G. Desai et al., "Dental Plaque: A Permanent Reservoir of *Helicobacter pylori?*" *Scand J. Gastroenterol*, 26, 1991, pp. 1205–1208.

K. Rosberg, "Adhesion of *Helicobacter pylori* to Human Gastric Mucosal Biopsy Specimens Cultivated in Vitro," *Scand. J. Gastroenterol*, 26, 1991, pp. 1179–1187.

Laura L. Zaika, "Spices and Herbs: Their Antimicrobial Activity and Its Determination," *Journal of Food Safety*, Sep. 1988, pp. 97–118.

Enno Hentschel et al., "Effect of Ranitidine and Amoxicillin Plus Metronidazole on the Eradication of *Helicobacter Pylori* and the Recurrence of Duodenal Ulcer", *The New England Journal of Medicine*, vol. 328, No. 5, pp. 308–312.

David Y. Graham, M.D., "Treatment of Peptic Ulcers Caused by *Helicobacter Pylori*", *The New England Journal of Medicine*, vol. 328, No. 5, pp. 349–350.

Walter L. Peterson, M.D., "*Helicobacter Pylori* and Peptic Ulcer Disease", *The New England Journal of Medicine*, vol. 324, No. 15, pp. 1043–1047.

Y. Glupczynski, "Use of a Urea Breath Test versus Invasive Methods to Determine the Prevalence of *Helicobacter Pylori* in Zaire", *Eur. J. Clin. Microbiol. Infect. Dis.*, Apr. 1992, vol. 11, No.4, pp. 322–326.

C. Lens–Lisbonne et al., *Chem. Abstract*, 108:52692v, vol. 108, 1988.

A. Pizsolitto et al., *Chem. Abstract*, 86:12226s, vol. 86, 1977.

S. Gocho, *Chem. Abstract*, 116:37816k, vol. 116, 1992.

*Primary Examiner*—John W. Rollins
*Attorney, Agent, or Firm*—Morgan & Finnegan

[57] ABSTRACT

The invention relates to the use of either an aqueous extract or an organic extract of the plant Thymus to prepare a pharmaceutical composition useful to inhibit the growth of *Helicobacter pylori* and the urease activity of *Helicobacter pylori*. In case of an aqueous extract, a minimum amount of 0.5 mg of the dry plant in the extract is required but the preferred amounts are above 1.2 mg. The aqueous extract may be used either as a drink, with or without additional ingredients, or transformed into a capsule or a paste. The invention also relates to in-vitro methods for inhibiting the growth of the urease activity of *Helicobacter pylori*.

9 Claims, 4 Drawing Sheets

THERAPEUTIC APPLICATION OF A THYME EXTRACT AND IN - VITRO METHODS FOR INHIBITING THE GROWTH AND UREASE ACTIVITY OF HELICOBACTER PYLORI

This application is a continuation-in-part of application Ser. No. 07/945,376 filed on Sep. 16, 1992, now abandoned.

The present invention relates to a new therapeutic application of a plant extract, more precisely of an extract of Thymus to prepare a pharmaceutical composition useful to inhibit the growth of pathogenic bacteria. More particularly, the invention relates to the use of said extract to prepare a pharmaceutical composition useful to inhibit the growth of *Helicobacter pylori* and urease activity of *Helicobacter pylori*.

BACKGROUND OF THE INVENTION

*Helicobacter pylori*, a bacteria isolated in 1982 from the stomach of patients with gastritis lesions and peptic ulceration, is a genus which formerly was related to Camphylobacter. It appears as a curved or S shaped gram-negative bacillus, its cell wall being smooth adhering closely to the cytoplasmic membrane. To-day, it is recognized that the grade of *Helicobacter pylori* colonisation is associated with chronic gastritis and peptic ulceration. It is the general conclusion that the presence of *Helicobacter pylori* colonisation is of great importance in both the development and chronicity of peptic gastric ulcer disease. It was reported that, more than 80% of cases of chronic gastritis and duodenal ulcer are associated with coexisting *Helicobacter pylori* infection and both are related to the development of the ulcer disease.

The routine treatment against *Helicobacter pylori*, is based on the use of bismuth subcitrate and antibiotics. However, as known this method does not eradicate *Helicobacter pylori* infection, and after a period of time the infection reoccurs.

Bismuth preparations were successfully used to combat various gastrointestinal disorders. The most commonly used are bismuth subsalicylate and colloidal bismuth subcitrate. Later on, combinations of bismuth salts with antibiotics, such as amoxycillin and metrodinazole, were also suggested. It was demonstrated that colloidal bismuth subcitrate improved dyspepsia by clearing the bacteria and not by any other effect of the drug on the gastrointestinal tract. To-day, it is considered that a triple therapy of:

(1) a bismuth compound;

(2) a nitroimidazole antibiotic, and (3) tetracycline or amoxycillin, is effective in eradicating *Helicobacter pylori* infection in most patients. However,it was pointed out that a long-term follow-up is required in order to determine whether a recurrence of histologic gastritis symptoms will not appear. Also it is known that some diarrhea effects might occur due to Clostridium difficile colitis. On the other hand, some complaints of constipations were also reported after treatments with bismuth subcitrate alone.

According to a very recent report (Rosberg K. et al. Scand. J. Gastroenterol 1991, 26 p. 1179–1187) tests which were carried out on pigs show that a good correlation exists between adhesion of *Helicobacter pylori* to the gastric epithelium and gastritis, in-vivo and in-vitro infected specimens, using the same bacterial strains. This is a very important finding considering the fact that the adhesion of *Helicobacter pylori* to pig gastric mucosal specimen is quite similar to the human condition. In another recent paper (Desai H. G. et al. Scand J. Gastroenterol 1991, 26, 1205–8) it is reported that there is a relationship between the two reservoirs of *Helicobacter pylori*, i.e. dental plaque and the stomach. Using the Camphylobacter-like organism test, *Helicobacter pylori* was detected in dental plaque and in gastric antral and body mucosa of a number of patients with dyspepsia. It was found that the density of *Helicobacter pylori* is heaviest in dental plaque and less in the body mucosa of the stomach. The treatment by the triple drug system (bismuth, nitroimidazole and amoxycillin) shows that the bacteria was eliminated from the gastric mucosa, in all the 24 patients treated, but persisted in dental plaque in all of them. The authors concluded that the dental plaque is a major reservoir of *Helicobacter pylori*, being greater in their number than in the stomach and may be responsible for the reoccurence of infection after cessation of therapy in the body mucosa of the stomach.

The above brief review clearly illustrates the potential diseases imparted by the *Helicobacter pylori* and the various approaches suggested to combat this bacteria.

It is an object of the present invention to provide a method for inhibiting the growth of *Helicobacter pylori*.

It is another object of the present invention to provide a method for inhibiting the growth of *Helicobacter pylori* without utilizing any of the known drugs or antibiotics.

It is a further object of the present invention to provide a method for inhibiting the growth of urease *Helicobacter pylori*. It is yet another object of the present invention to provide a method for inhibiting the growth of *Helibacter pylori*, which does not impart any undesired effects.

DESCRIPTION OF THE INVENTION

According to a first aspect, the invention relates to the use of an extract, in particular of an extract solution, of the plant Thymus to prepare a pharmaceutical composition useful to inhibit the growth of *Helicobacter pylori* bacteria in a host containing same. The above composition which is administered to the host contains an extract solution of the plant Thymus, the extract of the plant Thymus, being in an amount that is sufficient to inhibit growth of the bacteria in the host. The solution provided may be either in the form of an extract solution of said plant administered in the form of a drink solution or a capsule.

Thymus, also named Thyme, is a well known plant growing in many places. There are known three species of Thyme: *Thymus citriodorus, Coridothymus capitatus* and *Thymus vulgaris* and all of them were found to possess the above beneficial effect against this bacteria. It was surprisingly found that other plants, which are known as medical plants and are quite similar to Thyme, such as Camomile, Garlic, Olive rape, do not possess at all this property, or only to a unsignificant extent. Furthermore it should be pointed out that extracts of the above medical plants are mentioned in the literature to possess a medicinal property and are even suggested against disturbances in the digestion system.

According to a second aspect, the invention relates to a method to inhibit in-vitro the growth of *Helicobacter pylori* bacteria by contacting said bacteria with an extract, in particular an extract solution of the plant Thymus.

Figure 1:
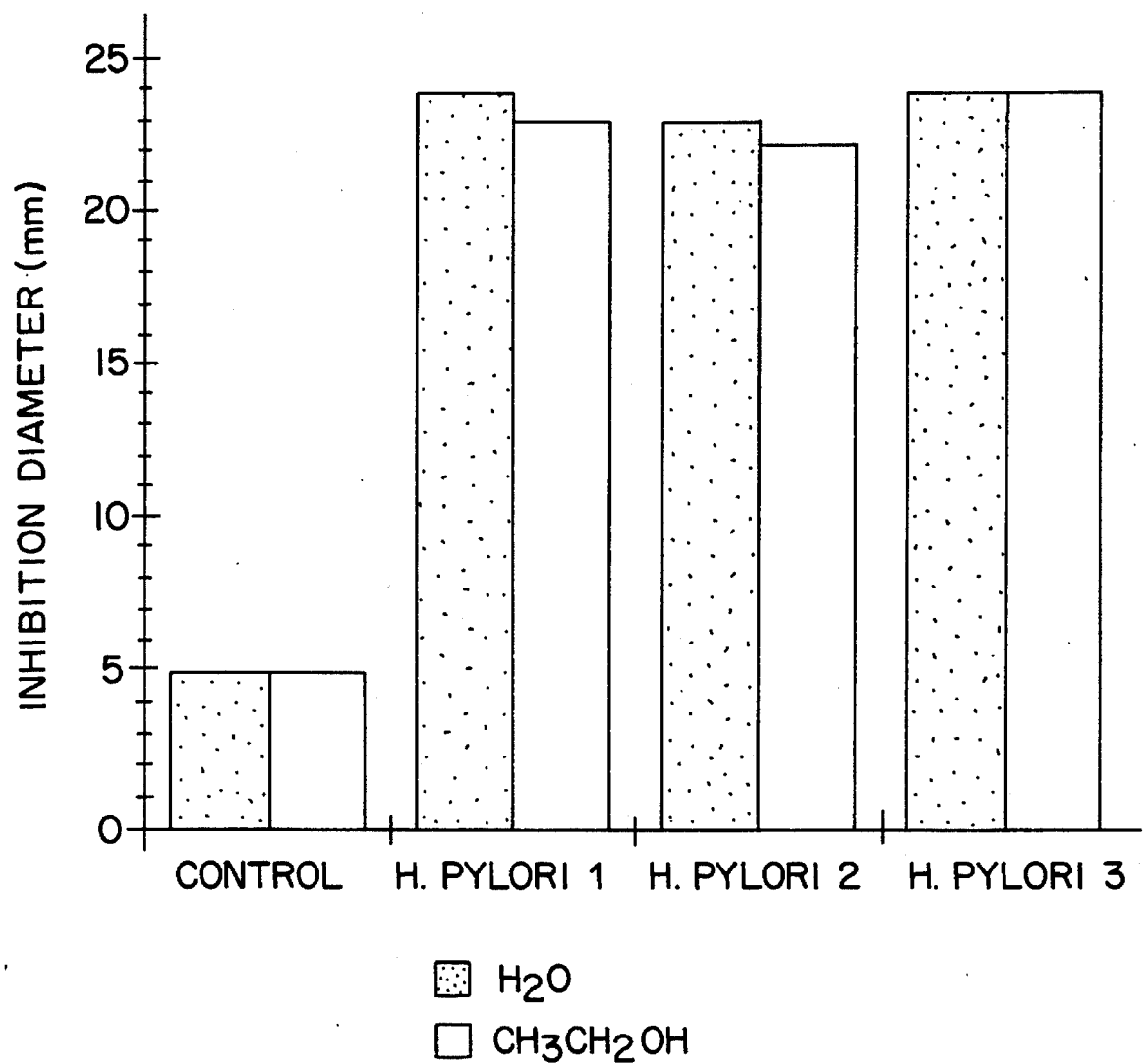
FIG. 1 is a graph showing the inhibition effect (as a function of the inhibition diameter of a disc containing *Helicobacter pylori*) of aqueous and alcohol thyme extracts on three isolates of *Helicobacter pylori* using the filter paper disc diffusion method.

The method was tested in-vitro on the various isolates of *Helicobacter pylori* which were mentioned as: 1, 2 and 3, and with all of them the same beneficial effect of growth inhibition was found. This appears in a clear manner from FIG. 1, where the inhibition effect of aqueous and alcohol Thyme extracts is illustrated towards three main species of *Helicobacter pylori*. This is an additional advantage over certain antibiotics which are not active on these bacteria.

The inhibition activity of an aqueous extract of Thyme was tested on three isolates of *Helicobacter pylori* ($I_1$, $I_2$, and $I_3$) obtained from various patients and significant inhibition effects were noticed for the three isolates substantially at the same extent. On the other hand, it can be noticed in the attached Table 1, that some of these types of bacteria were not found to be affected by some known antibiotics substances.

TABLE 1

Behaviour of antibiotic substances to three isolates of *Helicobacter pylori*.

| Type of the bacteria | Sensitive to | Not affected by. |
|---|---|---|
| $I_1$ | ampicyline | ceptarin |
| $I_2$ | nalidixic acid | erytromycin |
| $I_3$ | erytromycin | nalidixic acid |

The inhibition effect was determined in-vitro, using the "Filter paper disc diffusion method" as described by Laura L. Zaika, (Journal of Food Safety 9,1988, p. 97–118). According to the method used, an extract of a plant was deposited on a small filter paper disc having a diameter of 0.5 cm and then placed in the center of a Petri plate containing agar growth medium inoculated with the test microorganism. The plate was incubated under microaerophilic conditions in anaerobic jars at 37° C. for 3–5 days and observed for microbial growth. If the extract of a plant exerts antimicrobial activity, the microorganism will not grow in an area surrounding the filter paper disc. This clear area, defined as "zone of inhibition" was measured and recorded in mm. This method is well-known also for determining the activity of an antibiotic compound, by measuring the zone of inhibition arround a disc containing a sample of the antibacterial compound to be tested.

The assay used for the bacterial growth inhibition was as follows:

Equal concentration (dry substance 0.0027 g) of the Thyme extract from the three species were spotted on standard discs and placed on Egg Yolk Emulsion agar plate center which was previously layered with 0.1 ml bacterial suspension (concentration $10^7$ CFU/ml). Following the requessted incubation, the inhibition zone was recorded.

Figure 2:
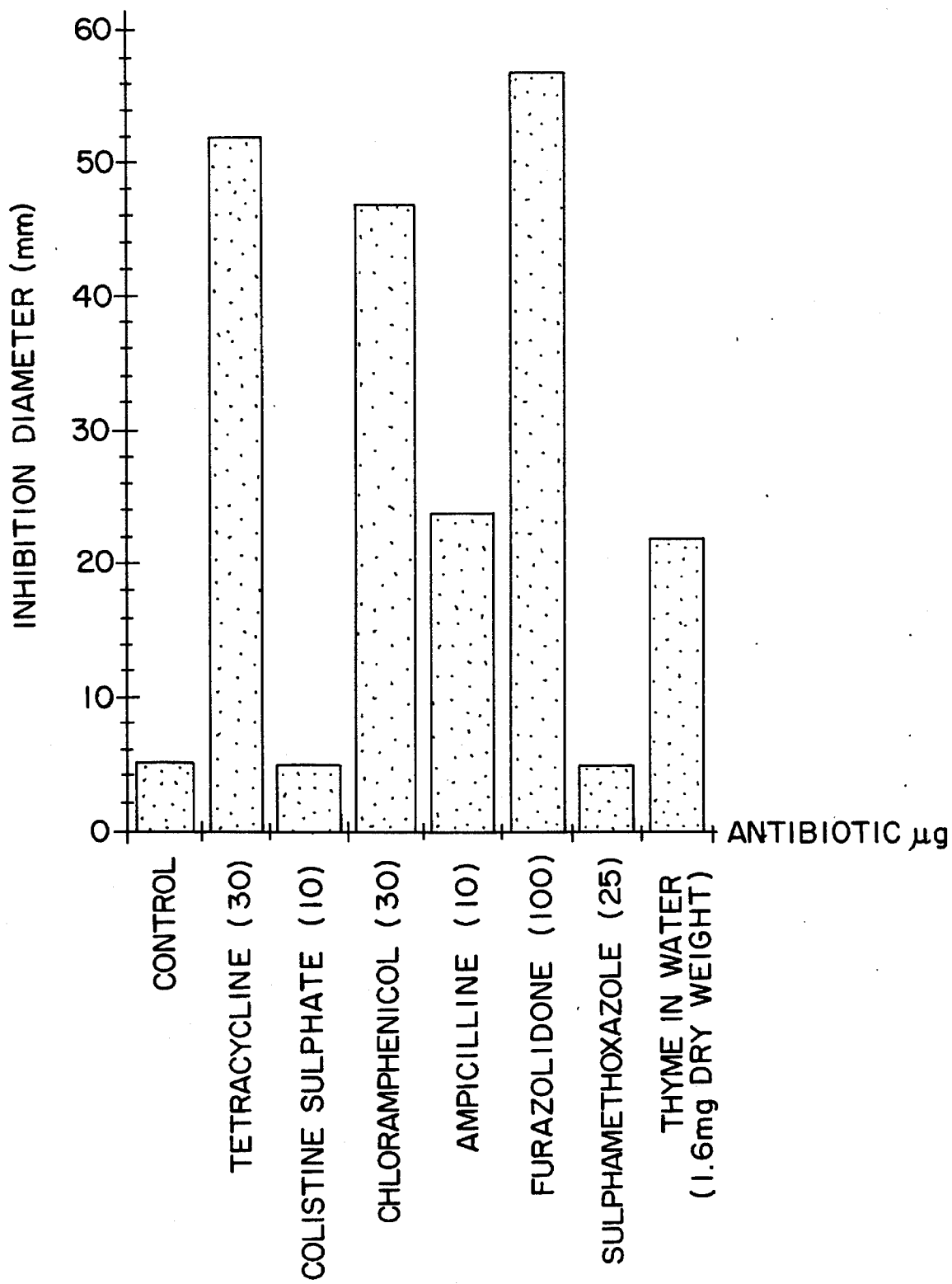
FIG. 2 is a graph showing the sensitivity (as a function of the inhibition diameter of a disc containing *Helicobacter pylori*) of *Helicobacter pylori* to antibiotics in-vitro and to aqueous thyme extracts using the filter paper disc diffusion method.

In FIG. 2, there are presented the sensitivity of *Helicobacter pylori*, as determined by the inhibition diameter, using an aqueous extract of Thyme (1.6 mg dry weight) compared with ampicilline (10 μg), sulphamethoxazole (25 μg) and colistine sulphate (10 μg), tetracycline (30 μg), furazolidone (100 μg) and chloramphenicol (30 μg).

The inventors are not yet in a position to explain why the inhibition activity of this bacteria is achieved only by the extract of Thyme. A possible explanation, might be the presence of 2-isopropyl-5-methyl phenol in this plant a constituent known for its antiseptic property, but of course other factors may also be involved.

Figure 3:
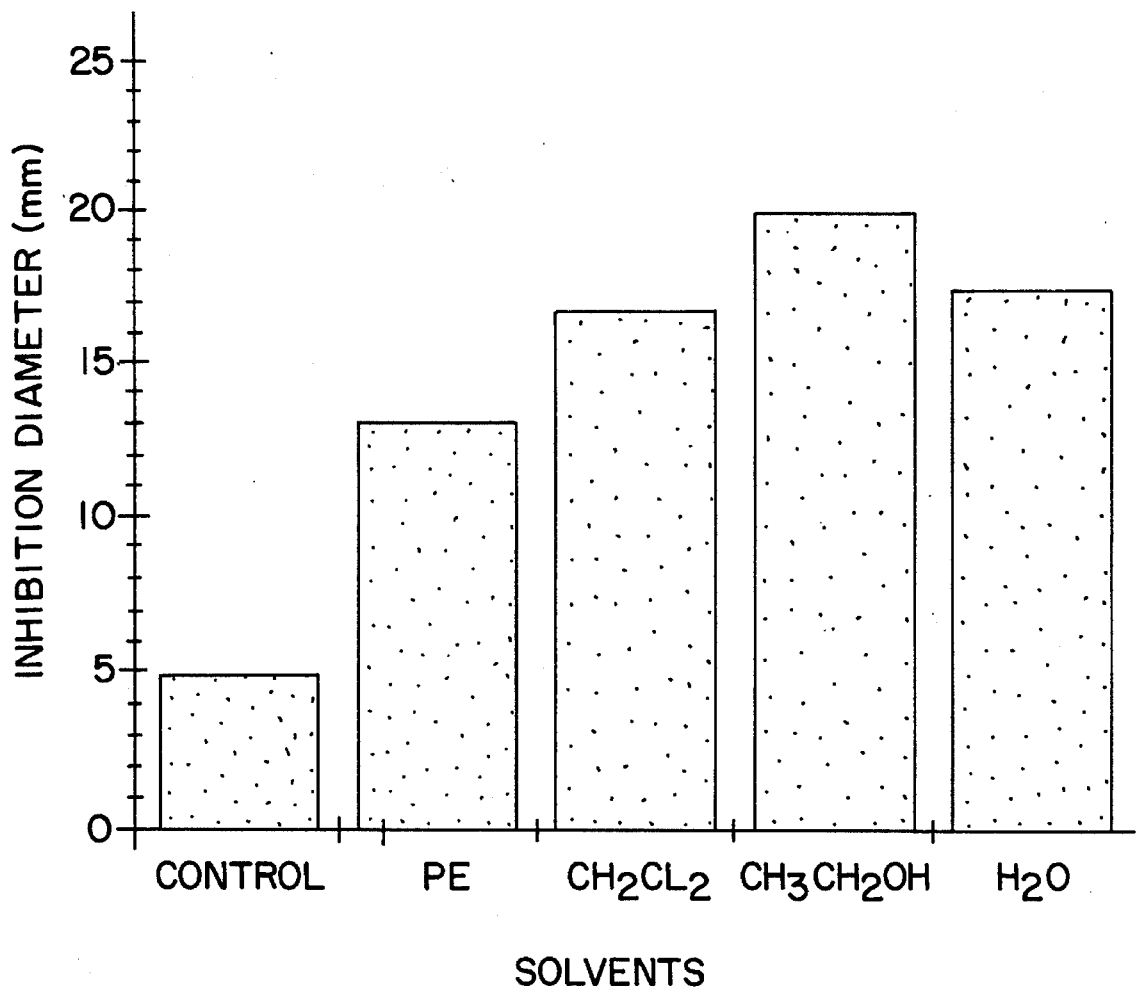
FIG. 3 is a graph showing the effect of various fractions of thyme, a petrol ether fraction, a methylene ether fraction and an ethanol fraction, on the inhibition diameter of a disc containing *Helicobacter pylori* using the filter paper disc diffusion method.

The extract of Thyme, was tested with aqueous and organic solvents, the latter being selected from a polar or non-polar solvent such as: ethanol, petrol ether, methylene chloride, etc. In FIG. 3 are presented the effect of a Thyme aqueous extract and of several solvents extract on inhibition diameter. It appears, that there is no any significant difference in the inhibition diameter from the various extracts. The aqueous extract has a significant advantage since it can be provided as a drink, with or without any additional taste ingredient. One may also conceive to prepare the dry plant pressed in the form of a capsule or a paste, which also would impart the same inhibition effect on the growth of *Helicobacter pylori*.

Figure 4:
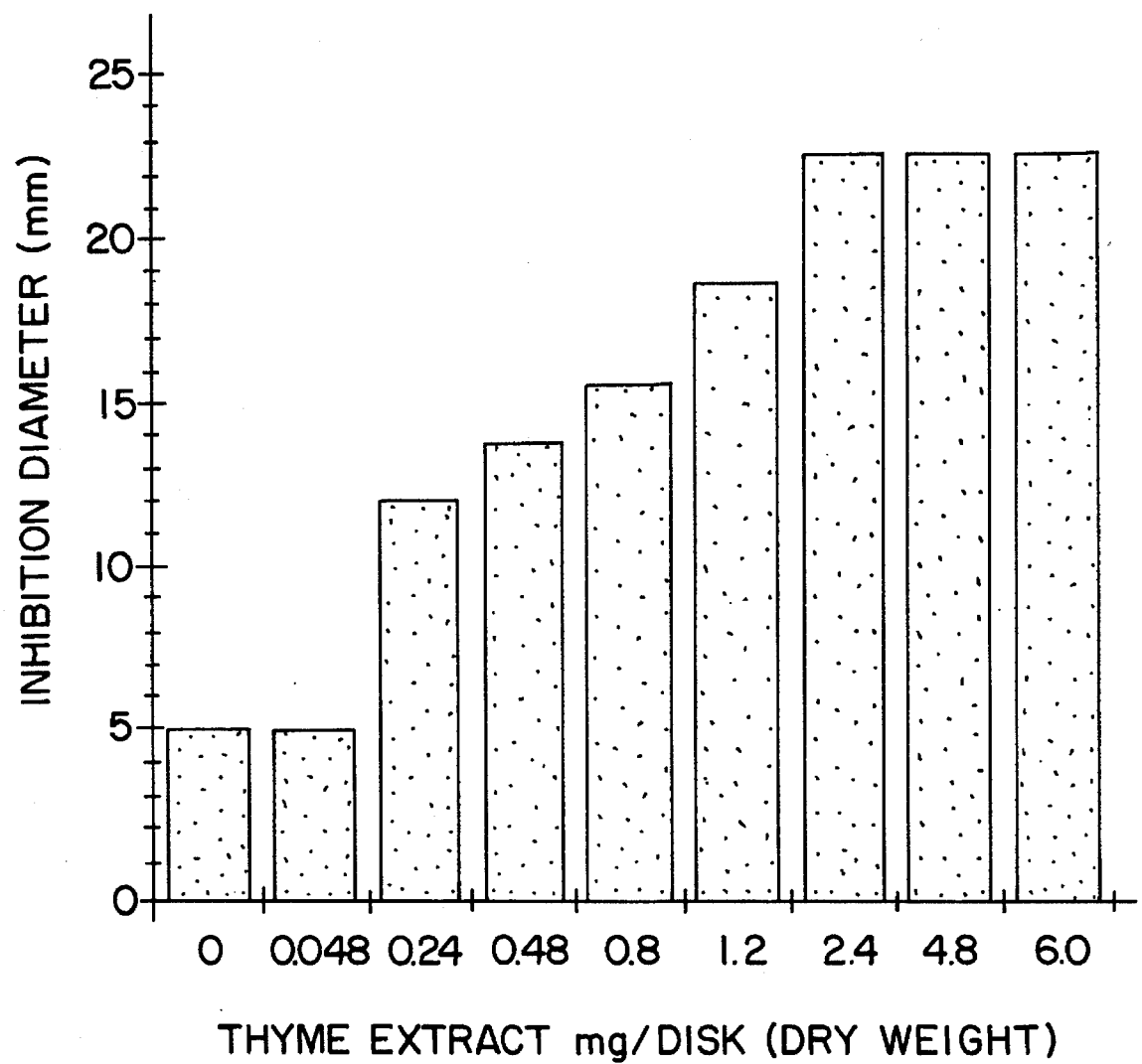
FIG. 4 is a graph showing the inhibition effect of from 0 to 6.0 mg/disc (dry weight) of aqueous thyme extract on the inhibition diameter of a disc containing *Helicobacter pylori*.

In case of an aqueous extract,it was found that a minimum amount of 0.5 mg of the dry Thyme should be present in the extract in order to impart some inhibition. A preferred amount should be above 1.2 mg when an inhibition diameter of about 18 mm was obtained. Above this amount there is a corresponding increase in the extent of the diameter inhibition, while above 2.4 mg of the dry plant in the extract there is no any change. This is clearly illustrated in the attached FIG. 4.

Another factor involved in the pathogenic mechanism of the bacteria, is urease of *Helicobacter pylori*. As known, the hydrolysis of urea and formation of ammonia, enables the bacteria to resist the acidity which prevails in the stomach. The urease of *Helicobacter pylori* is well-known as a pathogenic factor and therefore, its inhibition is indeed a long-felt need. There are known several chemicals, which are described in the literature to possess an inhibitory effect against urease of *Helicobacter pylori*. Among these chemicals the following reagents can be mentioned: aceto-hydroxamic acid, hydroxyurea, ethylene diamine tetraacetic acid and Lysine hydroxamate. The amount of these reagents for producing an inhibition of 50% from the enzyme activity is in the range of 0.06 to 0.1 g/l. According to the present invention, it was found that extracts of Thyme possess also an inhibition activity against *Helicobacter pylori* urease. Even an aqueous extract which contained 9 mg/ml of dry Thyme, was found to inhibit up to 65% of the urease activity of whole bacterial cells and at the same extent of bacterial lysates.

This was determined using a modified method of Conway as follows:

The reaction mixture contained:

2 ml of phosphate saline (3 mM), with a pH of 6.8.

0.4 ml of urea (330 mM), and 0.1 ml of a solution of urease *Helicobacter pylori* (possessing an activity of 483 μg $NH_4$/min/mg protein).

Thyme extracts were added to this reaction mixture in equal concentrations (dry substance—33 mg/ml). The time of reaction was 30 min. After the addition of a saturated solution of potassium carbonate, ammonia was absorbed by boric acid and finally detected by "Bertholet reaction". The results obtained are presented in the following Table 2 using various species of Thyme.

TABLE 2

*Helicobacter pylori* growth and urease activity in the presence of species of Thyme extracts

| Extract | Zone inhibition (mm). | Urease activity (%) |
|---|---|---|
| Blank | 0 | 100 |
| *Thymus citriodorus* | 12–13 | 35,9 |
| *Coridothymus capitatus* | 15–16 | 33,2 |
| *Thymus vulgaris* | 20–21 | 16,5 |

We claim:

1. A method of inhibiting the growth of *Helicobacter pylori* bacteria in a host containing same, which comprises administering to the host an extract solution of the plant Thymus, the extract of the plant Thymus being present in an amount that is sufficient to inhibit growth of the bacteria in the host.

2. The method of claim 1, wherein said Thymus is selected from the group consisting of *Thymus citriodorus, Coridothymus capitatus* and *Thymus vulgaris*.

3. The method of claim 1, wherein said extract solution is an aqueous extract of said plant.

4. The method of claim 3, wherein said extract solution is administered orally.

5. The method of claim 4, wherein said aqueous extract is administered in the form of a drink solution.

6. The method of claim 5, wherein additional flavoring ingredients are added to import a desired taste to said drink solution.

7. The method of claim 1, wherein said extract solution is administered in the form of a capsule.

8. The method of claim 1, wherein said extract solution is administered in the form of a paste.

9. A method of inhibiting urease activity of *Helicobacter pylori* bacteria in a host containing the same, which comprises administering to the host an extract solution of the plant Thymus, the extract of the plant Thymus being present in an amount that is sufficient to inhibit urease activity of the bacteria in the host.

* * * * *